United States Patent [19]

Chalifoux

[11] Patent Number: 5,312,253
[45] Date of Patent: * May 17, 1994

[54] DENTAL IMPLANT POST AND PROSTHESIS CONSTRUCTION

[75] Inventor: Paul R. Chalifoux, Wellesley, Mass.

[73] Assignee: Wellesley Research Associates, Inc., Wellesley, Mass.

[*] Notice: The portion of the term of this patent subsequent to Mar. 30, 2010 has been disclaimed.

[21] Appl. No.: 896,602

[22] Filed: Jun. 10, 1992

Related U.S. Application Data

[63] Continuation of Ser. No. 814,507, Dec. 30, 1991, Pat. No. 5,197,881.

[51] Int. Cl.⁵ ............................................. A61C 8/00
[52] U.S. Cl. .................................................. 433/173
[58] Field of Search ............... 433/172, 173, 174, 175, 433/176

[56] References Cited

U.S. PATENT DOCUMENTS

| | | | |
|---|---|---|---|
| 2,857,670 | 10/1958 | Kiernan, Jr. | 433/175 |
| 3,497,953 | 3/1970 | Weissman | 433/173 |
| 3,579,831 | 5/1971 | Stevens | 433/174 |
| 3,618,212 | 11/1971 | Weissman | 433/173 |
| 4,624,673 | 11/1986 | Meyer | 433/173 |
| 5,030,095 | 7/1991 | Niznick | 433/173 |
| 5,049,073 | 9/1991 | Lauks | 433/173 |
| 5,106,299 | 4/1992 | Ghalili | 433/172 |
| 5,122,059 | 6/1992 | Durr et al. | 433/173 |

FOREIGN PATENT DOCUMENTS 3300764  7/1984  Fed. Rep. of Germany ...... 433/173

*Primary Examiner*—John J. Wilson
*Attorney, Agent, or Firm*—Paul J. Cook

[57] ABSTRACT

A dental implant is provided for insertion into the jawbone of a patient for the purpose of building a dental prosthesis thereon. The implant includes a central hole for accommodating a dental post having slots and/or a key structure. The dental post slots fit over wings or allow wings/key structures to pass through in order effect retention while avoiding rotation of the positioned post.

33 Claims, 11 Drawing Sheets

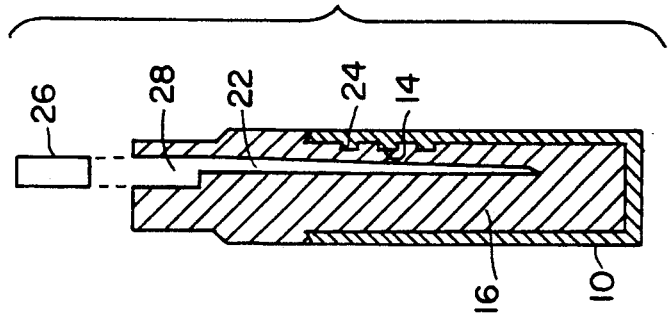
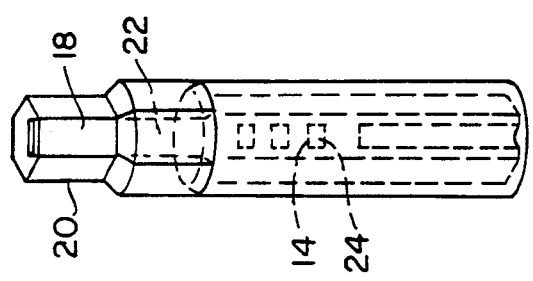
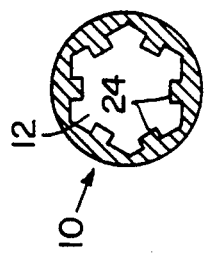
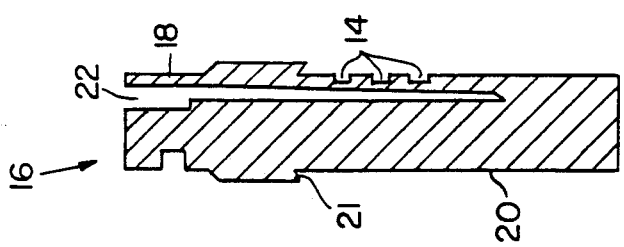
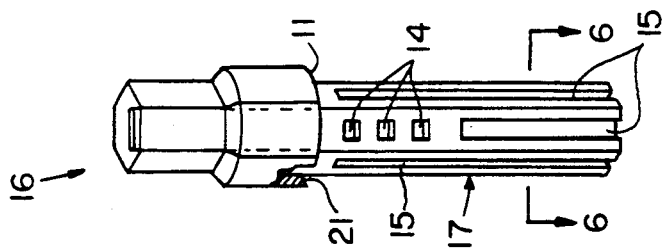
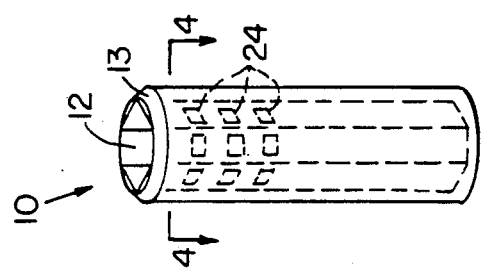

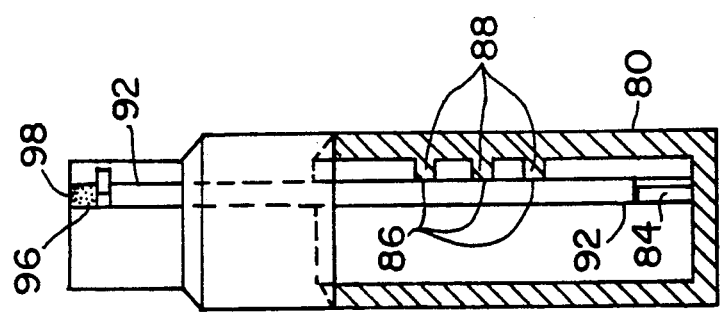
FIG. 15
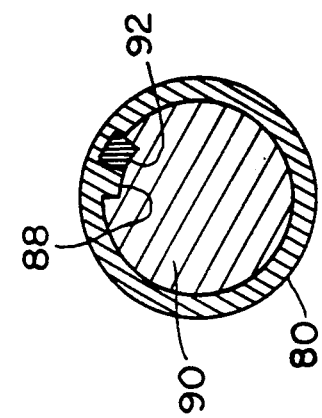
FIG. 16
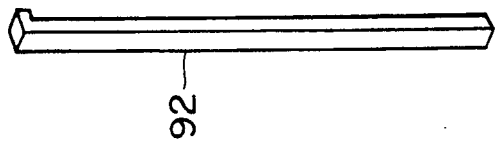
FIG. 14
FIG. 13
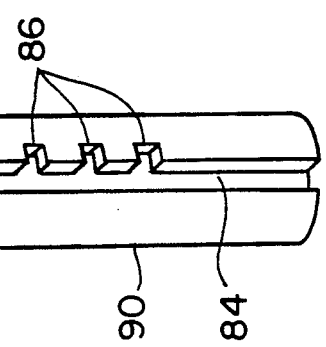
FIG. 12
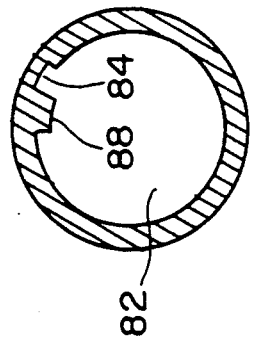
FIG. 11

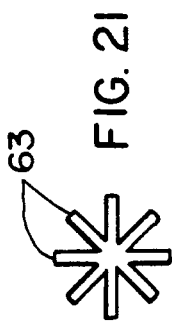
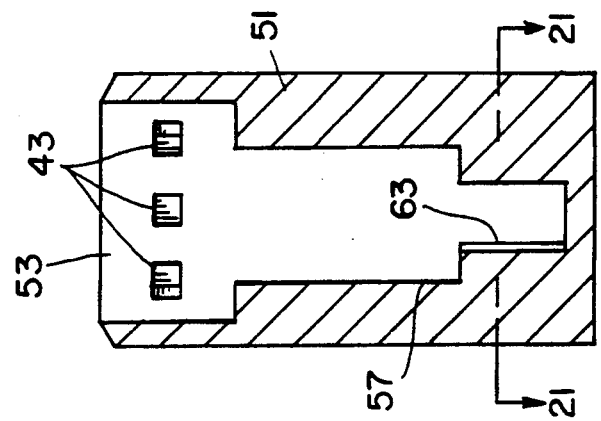
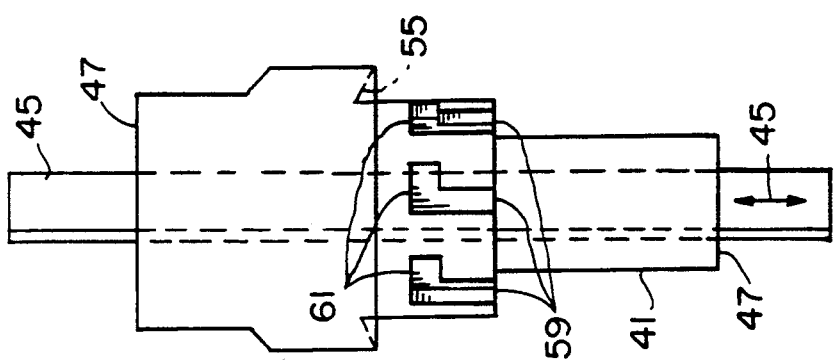
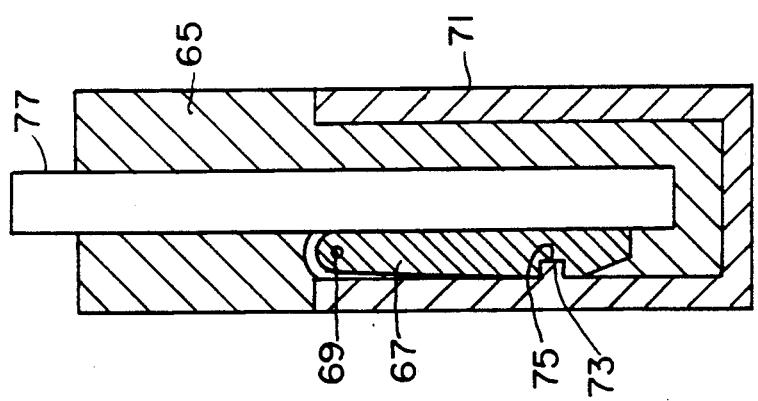
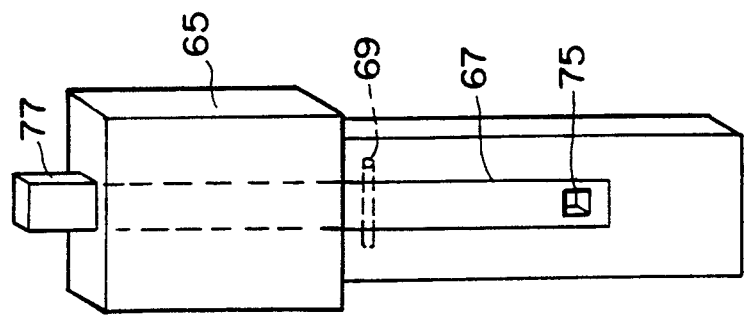

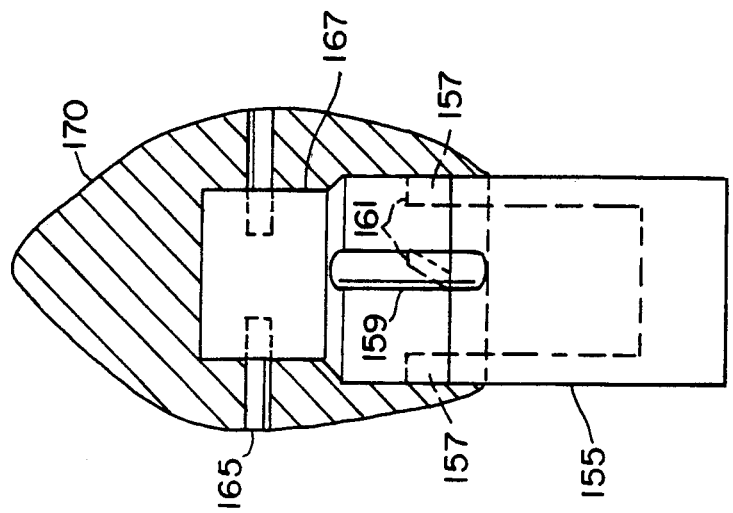
FIG. 32
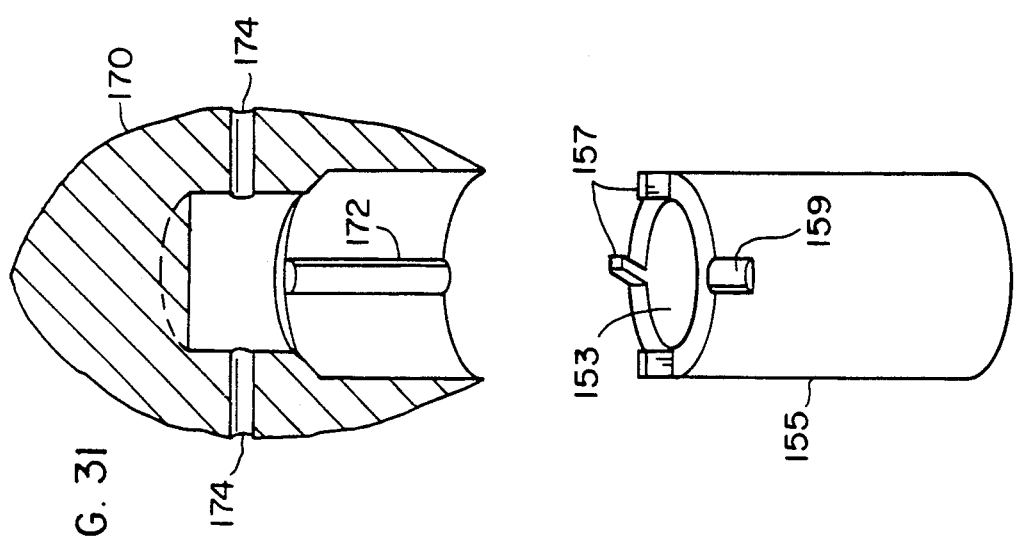
FIG. 31
FIG. 30
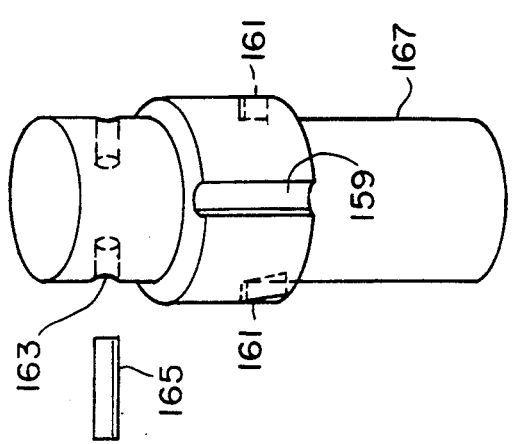
FIG. 29

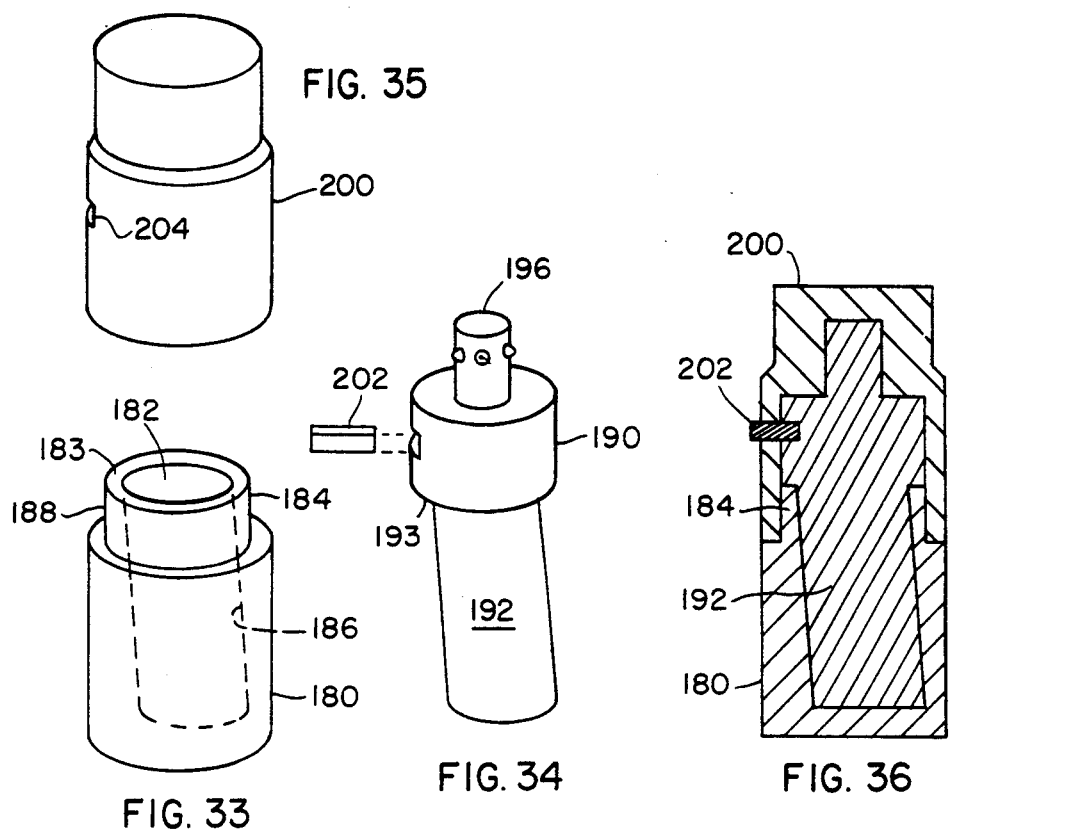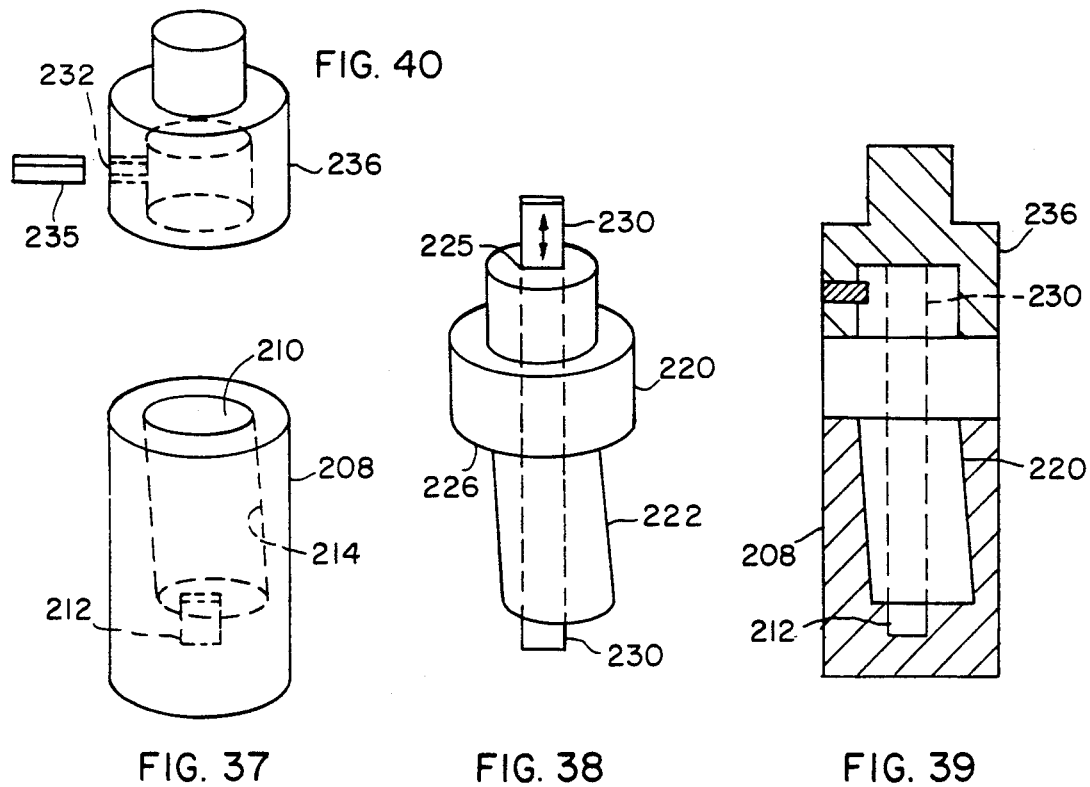

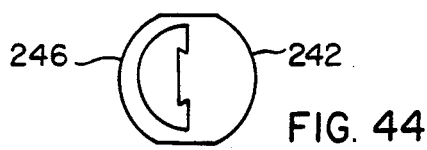
FIG. 44
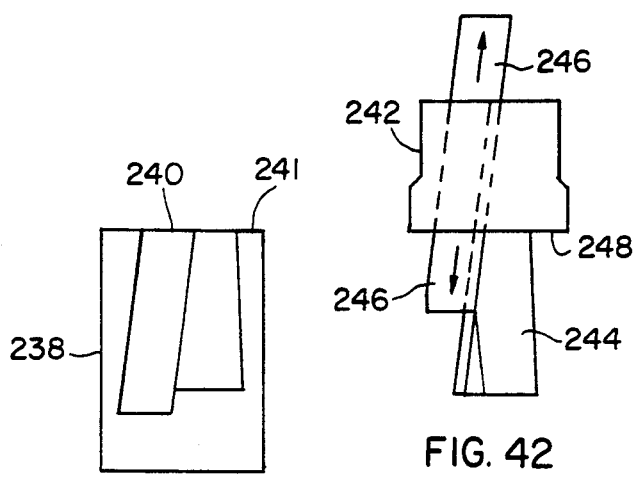
FIG. 41   FIG. 42   FIG. 43
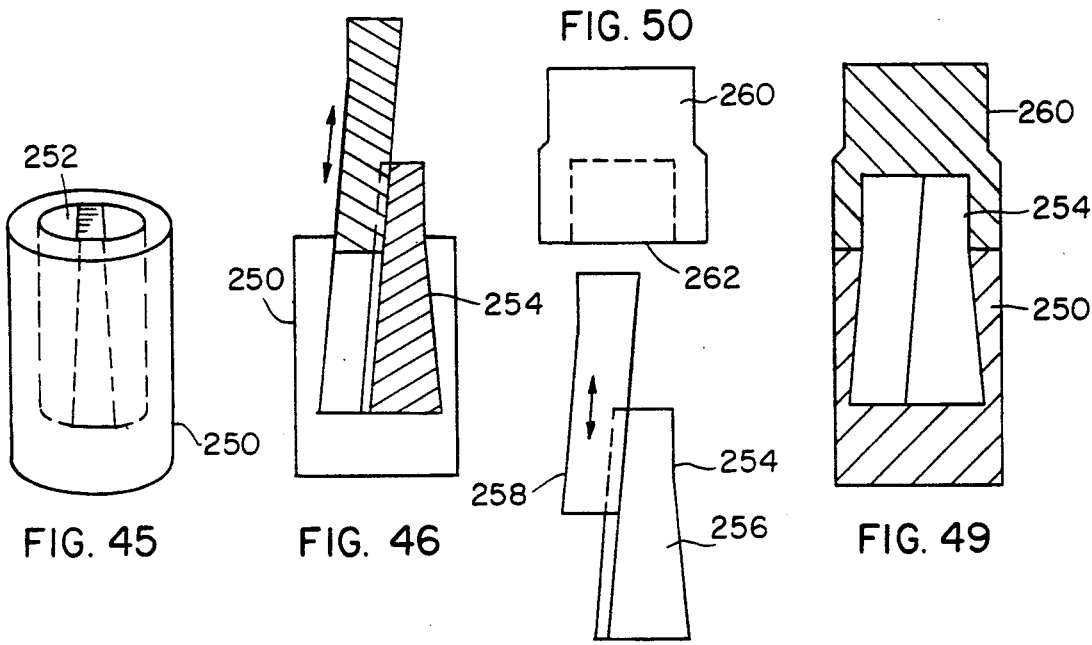
FIG. 45   FIG. 46   FIG. 47   FIG. 49
FIG. 50
FIG. 48

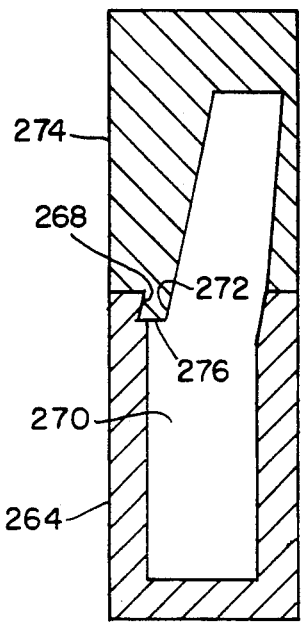
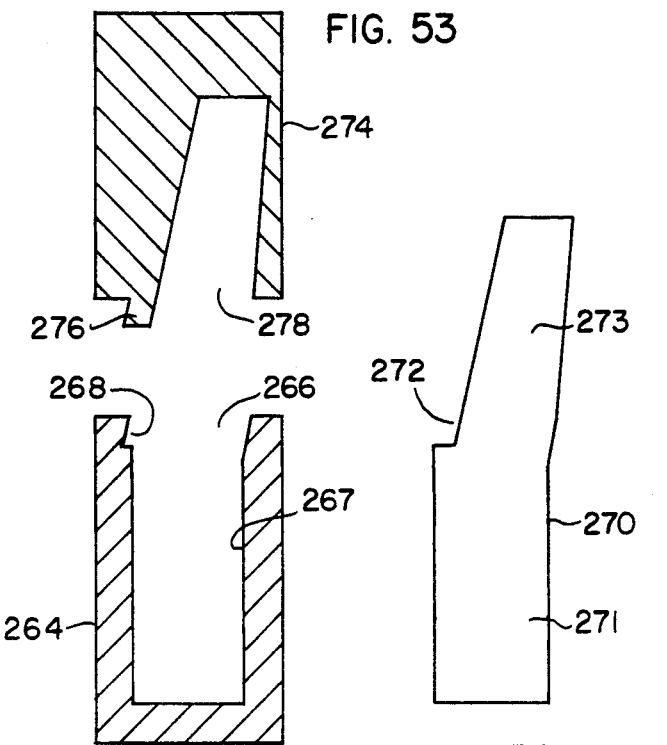
FIG. 53
FIG. 54   FIG. 51   FIG. 52
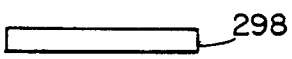
FIG. 58
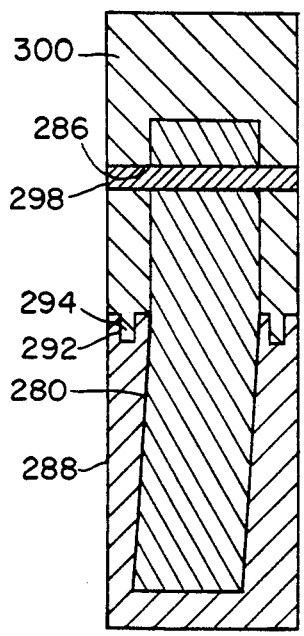
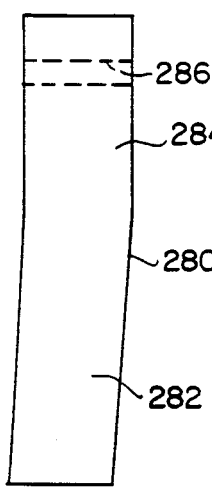
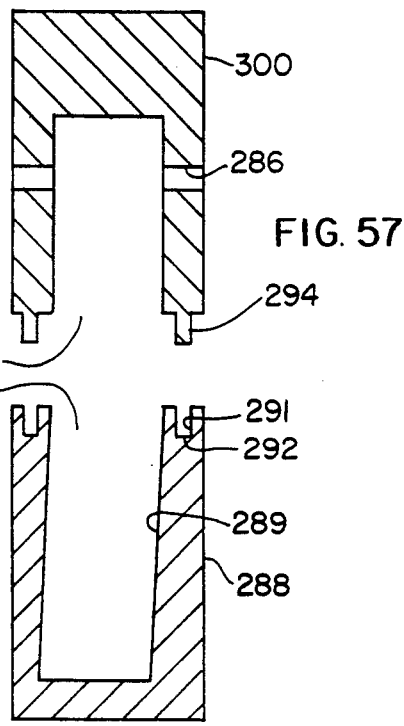
FIG. 59   FIG. 55   FIG. 56   FIG. 57

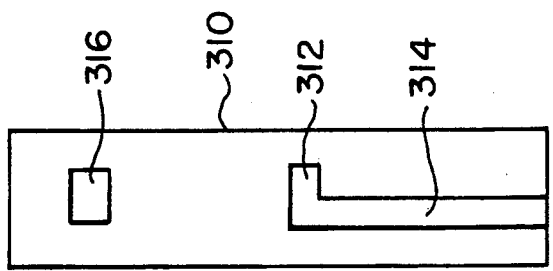
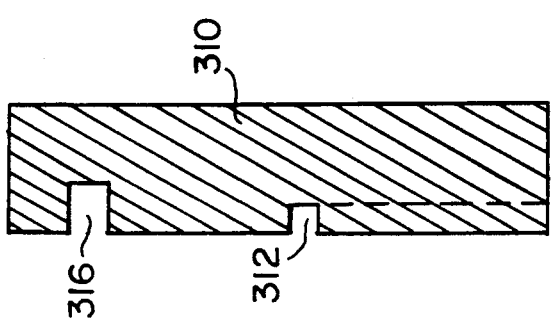
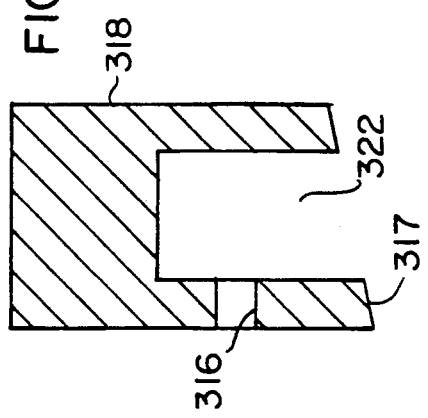
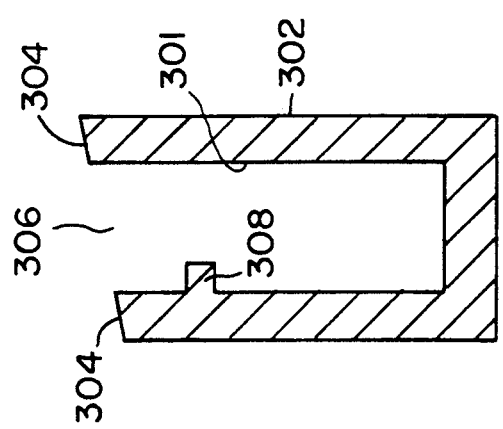
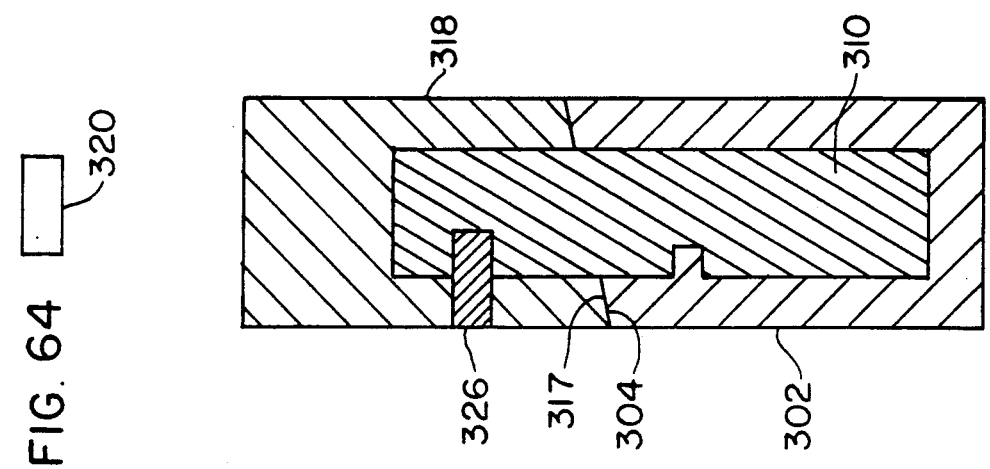

DENTAL IMPLANT POST AND PROSTHESIS CONSTRUCTION

REFERENCE TO RELATED APPLICATION

This application is a continuation-in-part of application Ser. No. 814,507, filed Dec. 30, 1991, now U.S. Pat. No. 5,197,881.

BACKGROUND OF THE INVENTION

This invention relates to a dental implant system which can be inserted into the jaw bone of a patient and can be utilized to improve retention of a dental restoration built onto the jaw bone.

Presently, dental implant systems are utilized to fix a synthetic tooth structure to the jaw bone of a patient in order to replace a missing tooth. The implant system includes an implant which is inserted into a hole in the patient's jaw bone drilled by a dentist. The implant includes a hole designed to receive a dental post which, in turn, serves to retain a core upon which a tooth crown is built. After the implant is inserted into the jaw bone, it is covered by the patient's gum and allowed to heal from 3-6 months while the bone grows to surround and retain the implant. The gum then is opened to expose the implant. At this time, impressions are made or a post needed to support the crown is positioned into the implant. At the present time, these posts are screwed into place with the implant heaving a helical path and the post having a mating helical thread. The post bottom can have threads or can have a hollow core for a screw to unite the post and implant. A screw system alone does not provide an antirotation characteristic to the implant system and can unscrew and loosen unless multiple screws are employed. A problem with this system is that the screws break during implacement and during function. Also, the screws are small and may be dropped in the mouth accidently or they are difficult to place into the back portion of the mouth. After the post is positioned in the implant, it extends above the gum so that a dental prosthesis including a core can be retained in place. All posts must resist normal rotational forces which occur during normal or abnormal functions. In general, preformed posts do not provide good stability against rotational force because they are round and rotate easily when placed in a round hole in the implant. Screw type posts can exert large lateral stresses which lead to potential implant fixture fracture and tooth loss. If filling material is placed around a preformed post above the jawbone to accept a crown after the post is positioned, the strength and long term stability of this material becomes a weak link in long term success of the crown. In addition, proper design of the post above the jaw line is critical to resist rotation or dislodging of the filling material from the post.

It has been proposed in U.S. Pat. Nos. 4,480,997; 4,490,116 and Re 31,948, to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far which will result in fracture. Furthermore, the radially outward forces of the legs on the tooth stub can result in fracture of the tooth stub over time. The same problems are present when these posts are used in conjunction with an implant positioned in a jaw bone.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental implant having a bore for a dental post which can be inserted into a hole in the jaw. In addition, it would be desirable to provide a dental implant with means to provide mechanical interaction in order to retain the post in the implant hole while minimizing or elimination forces on the implant walls exerted by the post. Furthermore, it would be desirable to provide a system for utilizing such a dental implant and post system which facilitates the placement of a core and a crown.

SUMMARY OF THE INVENTION

This invention provides a dental implant utilized in conjunction with a dental post in order to support a dental prosthesis. The implant is sized to be positioned within a hole of the jaw bone of a patient. The implant has an internal hole or bore of the implant such that the dental post cannot be rotated. The wall of the implant bore is provided with one or more wings or extensions which are shaped to engage one or more slots or indentations on the surface of the portion of the post which fits into the implant hole. Alternatively, the slot or indentation can be located on the bottom internal surface within which a key can fit. The key extends through the post and prevents the post from rotating. The key may also be used as a key and movable wing to prevent removal. The post slots can be positioned within the extensions or wings of the dental implant either by being moved radially or rotationally to engage the wings. When a plurality of slots are utilized in the post, they can be positioned at different vertical positions and/or different radial positions at the same or different vertical height. A dental post having slots that are moved radially into the wings includes one or more flexible legs each having a slot. These legs can be compressed radially inward so that the post can be positioned within the implant bore and the leg then can be allowed to expand so that the slot(s) cover and engage the wings in the implant. Alternatively, when the slots are rotated over the wings, they can be positioned over the wings of the implant by holes which start at the bottom of the post which interconnect with vertical paths in the post. The vertical paths, in turn, connect with the slots. The wings are inserted into the vertical paths and then rotated into the slots. Alternatively, when a slot extends from the top of the implant through the implant, it may exit to the side or bottom where a matching slot is on the bottom or side of the implant. A key or movable wing engages the slot in the post and in the side or bottom of the implant to prevent rotation or removal. A tight seal of the post to the implant may be accomplished through beveling, tight tolerances of a butt joint or O-rings.

To provide complete customization, as may be necessary in certain circumstances, copings are used which may be ground down or copings which may be cast to after impressions are taken. Finally, a prosthesis may be made removable by utilizing a separate series of slots and keys.

BRIEF DESCRIPTION OF THE DRAWINGS

FIG. 1 is an isometric view of an implant of this invention.

FIG. 2 is a front view of a post used with the implant of FIG. 1.

FIG. 3 is a side view of the post of FIG. 2.

FIG. 4 is a cross-sectional view taken along-line 4—4 of FIG. 1.

FIG. 5 shows the post of FIGS. 2 and 3 positioned into the implant of FIG. 1.

FIG. 6 is a cross-section of the bottom of the post in FIG. 2.

FIG. 7 is a side view of the post and implant of FIG. 5.

FIG. 11 is an implant used with the post of FIG. 13.

FIG. 12 is a top view of the implant of FIG. 11.

FIG. 13 is an isometric view of a post of this invention.

FIG. 14 is a key used with the post of FIG. 13.

FIG. 15 shows the post of FIG. 13, the key of FIG. 14 and the implant of FIG. 11 in place.

FIG. 16 is a cross-section of FIG. 15.

FIG. 17 is a front view of an alternative post useful with the implant.

FIG. 18 is a view of an alternative implant of this invention with the post of FIG. 17 in place.

FIG. 19 is an isometric view of a post of this invention.

FIG. 20 is an isometric view of an implant of this invention.

FIG. 21 is a cross-section view of taken along line 21—21 of FIG. 20.

FIG. 29 shows an alternatively post of this system.

FIG. 30 shows an isometric view of an alternative implant of this system.

FIG. 31 show an isometric view of a coping with a key external to the post and implant.

FIG. 32 shows a side view of the implant of FIG. 30, the post of FIG. 29 and the coping of FIG. 31.

FIG. 33 shows an isometric view of an alternative implant of this system.

FIG. 34 shows and isometric view of a post which is used in conjunction with the implant of FIG. 33.

FIG. 35 shows an isometric view of a coping used in conjunction with the implant of FIG. 33 and the post of FIG. 34.

FIG. 36 shows an cross-sectional view of the implant of FIG. 33, the post of FIG. 34 and the coping of FIG. 35 assembled.

FIG. 37 shows an isometric view of an alternative implant of this system.

FIG. 38 shows an isometric view of a post and key which is used in conjunction with the implant of FIG. 37.

FIG. 39 shows a cross-sectional view of the implant of FIG. 37, the post of FIG. 38 and the coping of FIG. 40 assembled.

FIG. 40 shows an isometric view of a coping used in conjunction with the implant of FIG. 37, the post of FIG. 38, and the key of FIG. 39.

FIG. 41 shows a cross section view of an alternative implant of this system.

FIG. 42 shows a cross-sectional view of a post and key used with the implant of FIG. 41.

FIG. 43 shows a cross-sectional view of the assembled implant of FIG. 41 and the post and key of FIG. 42.

FIG. 44 shows a cross sectional view of the top of the post and key of FIG. 42.

FIG. 45 shows an isometric view of an alternative implant of this system.

FIG. 46 shows a cross-sectional view of the post being placed into the implant of FIG. 46.

FIG. 47 shows a cross-sectional view of the post and key used with the implant of FIG. 45.

FIG. 48 shows a cross-sectional view of the post and key used with the implant of FIG. 45.

FIG. 49 shows a cross-sectional view of the implant of FIG. 45, the post and key of FIG. 47 and the coping FIG. 50 assembled.

FIG. 50 shows a cross-sectional view of the coping used in conjunction with the implant of FIG. 45.

FIG. 51 shows a cross-sectional view of an alternative implant of this system.

FIG. 52 shows a cross-sectional view of the post used with the implant of FIG. 51.

FIG. 53 shows a cross-sectional view of a coping used with implant of FIG. 51.

FIG. 54 shows a cross-sectional view of the implant of FIG. 51, the post of FIG. 52, and the coping of FIG. 53 assembled.

FIG. 55 shows a cross-sectional view of an alternative implant of this system.

FIG. 56 shows a cross-sectional view of the post used with the implant of FIG. 55.

FIG. 57 shows a cross-sectional view of a coping used with implant of FIG. 55.

FIG. 58 shows a cross-sectional view of a key used with the coping of FIG. 57.

FIG. 59 shows a cross-sectional view of the implant of FIG. 55, the post of FIG. 56, the coping of FIG. 57, and the key of FIG. 58 assembled.

FIG. 60 shows a cross-sectional view of an alternative implant of this system.

FIG. 61 shows a cross-sectional view of the post used with the implant of FIG. 60.

FIG. 62 shows a front view of the post of FIG. 61.

FIG. 63 shows a cross-sectional view of a coping used with implant of FIG. 60.

FIG. 64 shows a cross-sectional view of a key used with the coping of FIG. 63.

FIG. 65 shows a cross-sectional view of the implant of FIG. 60, the post of FIG. 61, the coping of FIG. 63, and the key of FIG. 64 assembled.

DESCRIPTION OF SPECIFIC EMBODIMENTS

Figure 10:
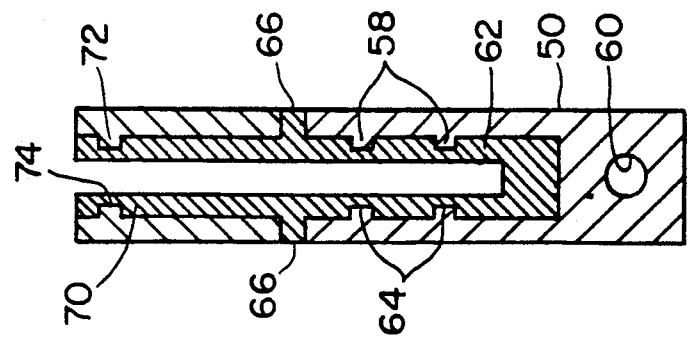
FIG. 10 is a cross-section view of an alternative implant-post-core system of this invention.

The dental implant of this invention includes a bore having at least one wing which permits locking a mating dental post having at least one slot into the implant without the need for screwing the post to place. By eliminating the use of a threaded screw, pressure on the implant is eliminated. The wings utilized in the implant or the slots in the post need not be of a continuous thread as would be necessary with a screw mechanism. The implant is utilized in conjunction with a dental post having a stem into which slots are placed. Alternatively, the slots may be placed above the stem and extending into the core with wings extending upward from the implant. The post and implant of this invention can be implanted under conditions to avoid the use of cement. Thus, the post can be removed, if desired, such as when an abscess occurs after implantation so that the abscess can be treated. The slots can be positioned over wings by moving a portion of the post radially into position or by rotating the post into position.

When a portion of the post is moved radially into position it is formed from a plurality of legs separated by a space. The legs can be radially compressed inward so that the slots can clear the wings in the bore or the implant. When the compression force is released, the legs resume a position so that they are essentially parallel to each other and the slots fit over the wings in the walls of the implant. The slots can be at the same or different heights. The slots can be the same or different sizes. The legs are not prestressed so as to avoid exertion of a force by the legs on the bore walls. By eliminating this stress in the legs, the implant fixture is not subjected to a continuous expansion force from within the implant. Therefore, the implant is less likely to fracture during normal use as compared to an implant containing a dental post that exerts a continuing expansion force on an implant.

In cases where the success of the implant is questionable, the post can be implanted without employing a dental cement in the post and implant. The wings mechanically lock the post in place, and together with a key structure described below, lock the post and supported crown in place when the crown is cemented over the post. The elimination of cement within the implant and post is advantageous since, with present technology, when an implant fails and a post is present, the post cannot be removed for retreatment to eliminate infection or if post fracture occurs, removal of the implant is necessary. When the post is removable, as in the case when cement within post and implant is not utilized, surgery can be avoided and the implant can be treated to eliminate infection. A key apparatus can be provided which fits into the space between the post legs. The key prevents flexing of the legs after the crown and core have been positioned on the dental post.

In the embodiment wherein the dental post is rotated into position with the implant, flexible legs in the dental post need not be included. The stem portion of the dental post can be formed of a unitary construction wherein slots are placed. The post is inserted into the implant bore so that the vertical pathways on the post which connect with the slots engage wings in the implant bore. When the wings have reached the same vertical position as the slots, the post is rotated so that the slots fit over the wings. The key can be inserted into the vertical pathways to prevent rotation of the post or the top surface of the implant can be angled relative to the path of insertion of the post.

In still another embodiment, wings may extend upward from an implant. A key may be external or internal to lock the system into position. The external key may be part of a coping or the crown constructed on it. In addition, the post shaft may be placed at an angle relative to the implant and locked by a coping or crown which has a different path of insertion going over the post and implant tabs. The tabs, however, may be part of the coping and the slots part of implant. A key can be used to lock a coping or crown onto the post-implant.

In still another embodiment, a coping is designed to fit over a post implant which is cast onto to form the final desired shape to construct a prosthesis on.

In still another embodiment, a post is placed in an implant and locked into position to prevent removal and rotation of the post by a key. The key has the shape of the internal bore of the implant to lock the post or use definitive slots on the side or bottom of the implant.

In still another embodiment, the prosthesis constructed on the implant/post is made removable by using a separate key and slot combination in which a key passes through a hole in the crown and into the post for retention. The key is held in by suction, friction, cement or threaded. The material forming the key will be of a soft consistency such that it may be drill out with ordinary dental drills. The key may be a hard material and be reversible by threading or friction with a continuous hole from one side to the other side such that the key may be pushed out one side from the other.

In still another embodiment, a coping is used for customization over an implant/post to construct a prosthesis. There are times when it is necessary to align copings to be parallel to other copings. The proposed copings are of two varieties. First, a coping may be made of a large size which can be hand trimmed to the appropriate smaller dimensions. Secondly, a coping may be made which fits precisely over an implant/post such that metal through a lost wax technique may be cast to it.

To aid in manufacturing tolerances for the fit of parts the post, key, coping, wings, slots and implant may use tapers, coating of metal with materials such as plastic, or bevels.

Referring to FIGS. 1 thru 7, the dental implant 10 formed from any suitable dental material includes a hexagonal bore 12 and wings 24. The wings may be of various sizes or the same size in relation to each other and are positioned at different vertical heights within the bore 12. The bore 12 can be of any desired shaped crosssection. The hexagonal shape permits positioning of a post in 6 different positions, for example. Of course, larger or smaller number of facets forming the bore shape can be used. The bore also can be circular, elliptical or the like. For convenience, the dental post 16 is shown with two legs 18 and 20. However, it is to be understood that up to eight legs can be formed conveniently with appropriate slots in stem section 22. The slots 14 are placed in leg 18 such as by conventional molding, machined or casting processes. There are slots 15 which extend from the bottom of the post 16 toward the top of the shaft 17. The dental post 16 is inserted into the implant 10 by placing the slots 15 in alignment with wings 24 of implant 10. Upon further placement, compressing flexible leg 18 radially inward so that the leg 18 and slots 14 clear the wings 24 of the bore 12 and so that the post 16 can be inserted completely into bore 12. After the post 16 is inserted, compression on the leg 18 is released and slots 14 are positioned onto the wings 24. Thereafter, a key 26 is inserted into space 28 so that the slots 14 are maintained over the wings 24. Once, the post 16 is inserted into implant 10, rotation is prevented.

The dental post can be made of a variety of sizes. For example, a dental post can extend about 3 to 18 mm into the implant and 1 to 7 mm above the jaw bone. A typical dental post diameter can vary between about 1.5 mm and 4 mm. The wings can extend a length away from the implant a distance between about 0.1 mm and about 1 mm while the slot can vary in width between 0.1 and 2 mm. It is to be understood that these dimensions are exemplary and will vary with the need of the patient. The sides may be parallel or tapered. The outside junction of the bottom of the post 11 to the implant top 13 may be may have a bevel 21 to provide a tight fit and less need for extreme tolerances of the wing 24 to the slot 14 in size.

Figure 8:
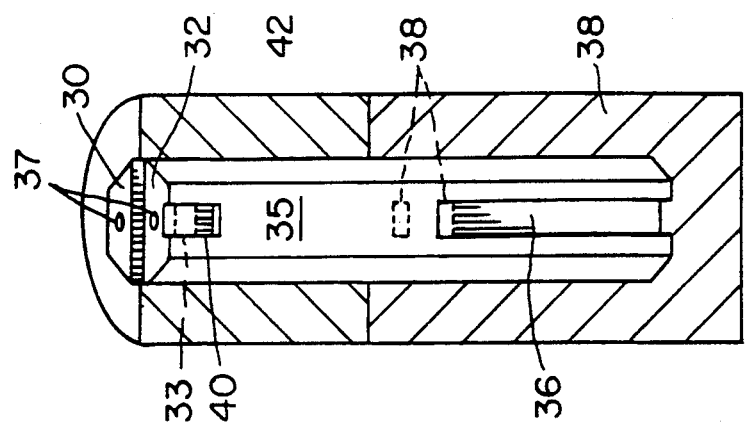
FIG. 8 is an isometric view of an implant-post-core system of this invention.

As shown in FIG. 8, the legs 30 and 32 of post 35 can have slots 36 which fit over wings of implant 38 and have slots 40 which fit over appropriately sized wings of a core or crown 42. The post 35 can be provided with holes 37 into which a tool can be inserted to assist in flexing legs 30 and 32 for insertion into implant 38.

Figure 9:
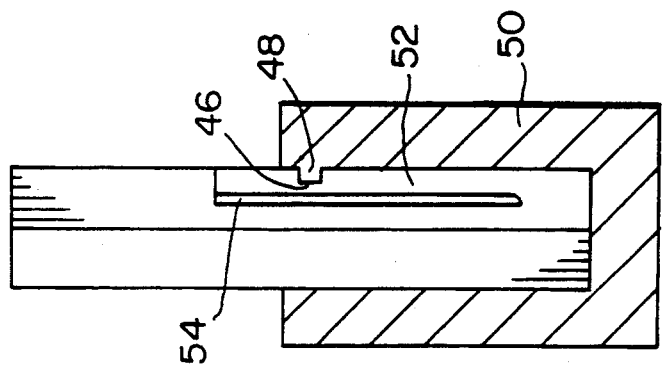
FIG. 9 is a side view of an alternative implant-post-core system of this invention.

Referring to FIG. 9, the post-implant system of this invention is shown with one slot 44 in post 46 and one wing 48 in implant 50. The leg 52 is sufficiently flexible so that slot 44 can be positioned into and away from wing 48 by compressing exposed area 54 or releasing area 54 from compression force.

As shown in FIG. 10 the implant 50 can be provided with a hole 60 for the purpose of allowing bone to grow into the implant 50. The post 62 is provided with slots 64 for insertion onto mating wings of implant 58. The post 62 also is provided with flanges 66 to position it on implant 58 as well as provide a solid seal to the implant. Extension 70 of post 62 has extension 70 to accommodate core 72. Extension 70 is provided with slot 74 which fits onto wings of core 72 after compression force on post 62 has been released form flanges 66. Thus, the post 62 can be utilized to position core 72 in proper position while eliminating the need for pressure on implant 58.

Referring to FIGS. 11–16, a system of this invention is shown which permits rotational implacement of the post of this invention into the implant of this invention. The implant 80 is provided with core 82 and vertical pathways 84 and wings 88 which are positioned at varying vertical positions. Pathways 84 permit insertion of post 90 so that wings 88 can be positioned into slots 86. Once so positioned, key 92 is positioned into the space and pathway 84 so that rotation of the post 90 is prevented. A cement 98 can be applied into spaces 94 and 96 to retain key 92 in place. Since the cement 98 is easily accessible after a core or crown (not shown) is to be removed, the key of 92 can be removed if it is desired to access the implant to treat infection after initial implant system is in place.

Referring to FIGS. 17 and 18 an alternative implant-post-key system of this invention is shown. The post 65 includes a leg 67 supported by a hinge 69. The implant 71 includes a hole having a rectangular cross-section. When the post is placed into the implant 71, the leg 67 swings about hinge 69 so that slot 75 of leg 67 is positioned over wing 73 of implant 71. Thereafter key 77 is inserted into central rectangular holes in post 65 and implant 71 to prevent rotation of post 65 and to stop the leg from swinging on hinge 69.

Referring to FIGS. 19, 20 and 21, an alternative implant-post-key system of this invention is shown. The post 41 includes a shoulder 55 slots 59 and a central rectangularly shaped hole to accommodate a vertically movable key 45. The key extends beyond both ends 47 and 49 of the post 41. The implant 51 includes a central hole 53 to accommodate post 41 so that surface 49 of post 41 contacts surface 57 of implant 51. The wings 43 are inserted into vertical pathways 59 and the post 41 then is rotated so that wings 43 are inserted into slots 61. The key 45 then is inserted through post 41 into the rectangular hole 63 so as to prevent rotation of post 41. The slot 63 may accommodate multiple rotational positions of key 45 through post 41.

Figure 23:
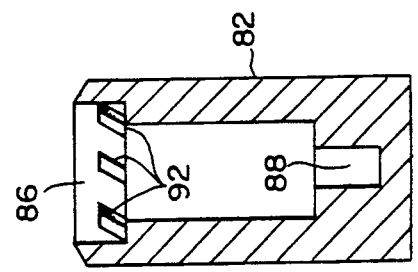
FIG. 23 shows an implant having angled tabs.
Figure 22:
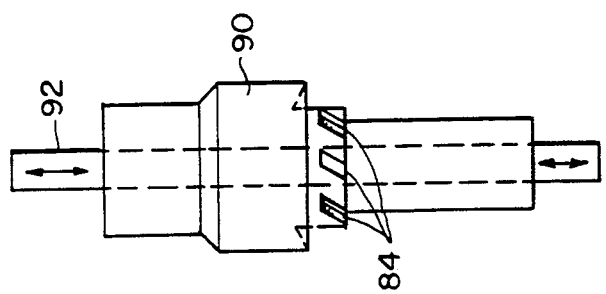
FIG. 22 shows a post and key which is used in conjunction with the implant of FIG. 23.

Referring to FIGS. 22 and 23, the implant 82 includes angled internal tabs 92, a central opening 86 and a key slot 88. The post 90 includes angled slots 84 which mate with angled tabs 92 when post 90 is rotated. After the tabs 92 are in position within slots 84, key 94 is inserted through the center of post 90 and into key slot 88 in order to retain the post 90 in place without the need for cement.

Figure 24:
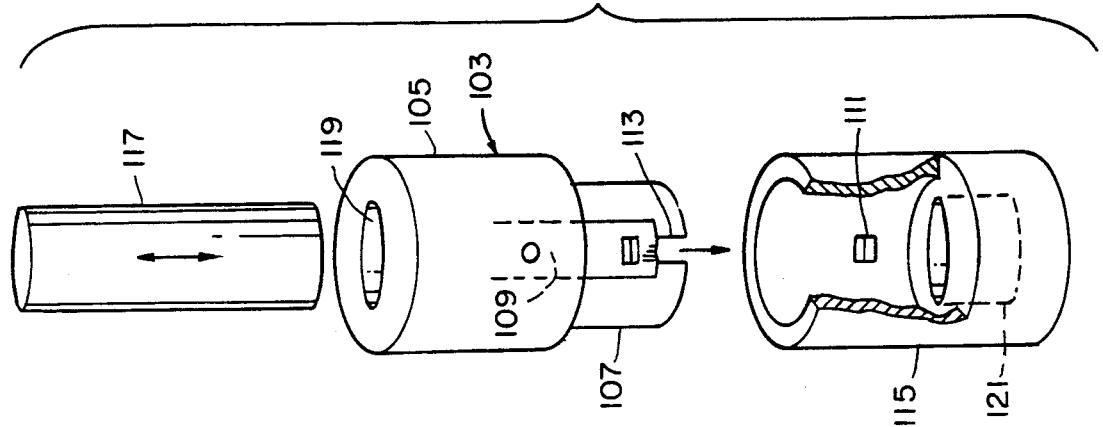
FIG. 24 shows an alternative post-implant system of this invention.

Referring to FIG. 24, the post 103 includes and upper section 105 and a lower section 107. A spring 109 is formed within the walls of sections 105 and 107. The spring 109 includes a slot 113 which fits over and extension or tab 111 of implant 115. The elliptical key 117 fits through the central opening 119 of post 103 and extends into slot 121 located on the lower internal surface of implant 115 to prevent rotation of post 103.

Figure 26:
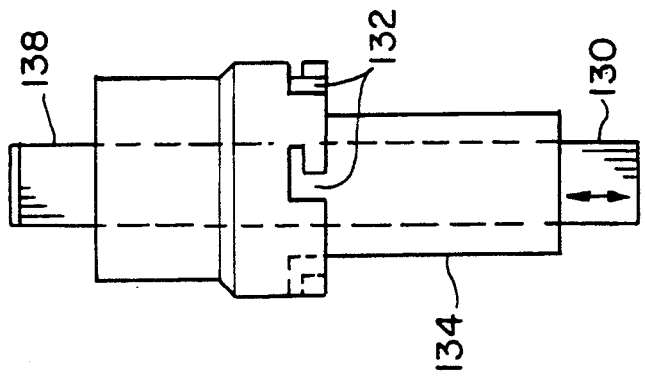
FIG. 26 shows a post and key which is used in conjunction with the implant of FIG. 25.
Figure 25:
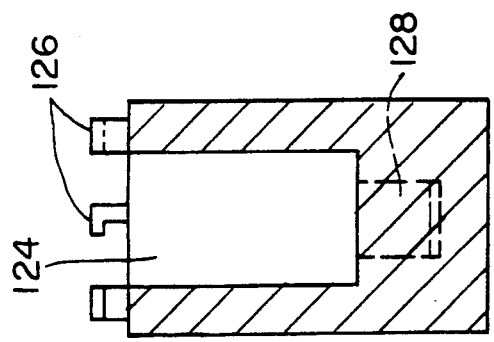
FIG. 25 shows an alternative implant of this implant with tabs which extend upwardly.

Referring to FIG. 25 and 26, the implant 122 includes a central bore 124, tabs 126 which extend upward from the implant 122 and at right angles and a key slot 128. The post 134 includes slots 132 which mate with tabs 126 when post 134 is placed and rotated. After the tabs 126 are in position within the slots 132, key 130 is inserted through the center of post 134 and into the key slot 128 in order to retain the post 134 in place without the need for cement. Key 130 and slot 128 may be angled for added retention of post 134.

Figure 28:
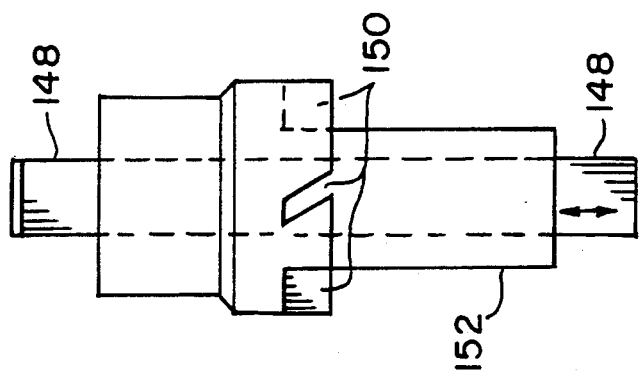
FIG. 28 shows a post and key which is used in conjunction with the implant of FIG. 27.
Figure 27:
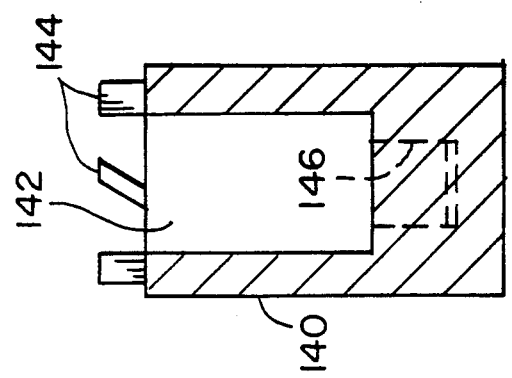
FIG. 27 shows an alternative implant system.

Referring to FIGS. 27 and 28, the implant 140 includes a central bore 142, angled tabs 144 which extend upward from the implant 140 and a key slot 146. The post 152 includes slots 150 which mate with tabs 144 when post 152 is placed and rotated. After the tabs 144 are in position within the slots 150, key 148 is inserted through the center of post 152 and into the key slot 146 in order to retain the post 152 in place without the need for cement.

Referring to FIGS. 29–32, the implant 155 includes a central bore 153, angled tabs 157 which extend upward from the implant 155 and an external key slot 159. External key slot 159 which may be concave, flat or convex of different radial curvature than the overall radial curvature of coping 170, stops rotation of coping 170. The post 167 includes slots 161 which mate with tabs 157 when post 167 is placed and rotated. After the tabs 157 are in position within the slots 161, key 172 which is part of a coping or crown is positioned over post 167 and implant 155 and into the key slot 159 in order stop rotation and to retain the post 152 in place without the need for cement. Coping or crown 170 has slot 174 through which is placed key 165. Key 165 further extends into slot 163 of post 167 to retain coping or crown 170.

Referring to FIGS. 33-36, the implant 180 includes a central bore 182 which goes at an angle in relationship to the overall implant 180 and upward tabs 184 such that the bore walls 186 are not parallel to the outside wall 188 of the tab 184. Tab 186 may by continuous or multiple individual, angled, right angled, etc. Post 190 has an angled shaft 192 in relation to the post head 196 in the same spatial and angular relationship as the implant tabs 184 to the bore wall 186 such that when post 190 is positioned with in implant 180 the shaft 192 of post 190 fits securely into bore 182 and surface 193 of post 190 fits flush with surface 183 of implant 180. After post 190 is in position in implant 180 coping 200 is positioned over post 190 and implant 180 in order to retain the post 190 in place without the need for cement. Coping or crown 200 has slot 204 through which is placed key 202. Key 202 further extends into slot 206 of post 190 to retain coping or crown 200.

Referring to FIGS. 37-40, the implant 208 includes a central bore 210 which is at an angle in relationship to the overall implant 208 and key slot 212 such that the bore wall 214 are not parallel to the sides of the key slot 212. Post 220 has an angled shaft 222 in relation to the post head 224 in the same spatial and angular relationship as the implant key slot 212 to the bore wall 214 such that when post 220 is positioned within implant 208 the shaft 222 of post 220 fits securely into bore 210 and surface 226 of post 220 fits flush with surface 228 of implant 208. After post 220 is in position in implant 208 key 230 is positioned into the key slot 212 of implant 208 in order to retain the post 220 in place without the need for cement. Coping or crown 236 has slot 232 through which is placed key 235. Key 235 further extends into slot 225 of post 220 to retain coping or crown 236.

Referring to FIGS. 41-44, the implant 238 includes a central bore 240 which is narrower at the top and wider at the bottom. Post 242 has a contiguous cylinder of which surface 248 rests on the top surface 241 of the implant 238. There is a key 246 which fits inside of post 242 and slides up and down. With the key 246 retracted, the post section 244 of post 242 can be seated. Upon positioning of post 242 into implant 238, key 246 is positioned in order to retain the post 242 in place without the need for cement.

Referring to FIGS. 45-50, is an alternative to the previously described implant system. The implant 250 has a central bore 252. Post 254 consists of two sections including a fixed section 256 and movable key 258. Fixed section 256 is positioned within the implant 250 through bore 252. Upon complete seating of fixed section 256, key 258 is positioned within implant 250. To prevent removal of key 258 and fixed section 256, a coping or crown 260 having slot 262 is positioned over post 254. The coping or crown 260 is held in position by cementing or by a lateral acrylic peg as described in earlier implant alternatives.

Referring to FIGS. 51-54, the implant 264 includes a central bore 266 with a wall 268 which is at an indented angle in relation to wall 267 which will form the side of a slot. Post 270 has a shaft 271 which fits securely into central bore 266 of implant 264, a wall 272 which forms a side of a slot and a body 273 which is at the same angle or less as wall 272 and wall 268 of implant 264 to allow placement of core 274. Core 274 has tab 276 which fits into the slot formed by wall 272 of post 270 and wall 268 of implant 264 when post 270 is placed in central bore 266 of implant 264. Core 274 has a central hole 278 which fits over post body 273 when assembled.

Referring to FIGS. 55-59, the implant 288 has a central bore 290 which is at an angle in relationship to the overall implant 288, a slot 292 which is angled in relation to the implant bore wall 289 such that slot wall 291 is not parallel to implant wall 289. Post 280 has a shaft 282 which fits securely into central bore 290 of implant 288, a body 284 which fits securely into central bore 296 of coping 300, a hole 286 which aligns with hole 286 of core 300 when body 284 of post 280 is fit into central bore 296 of core 300. Core 300 has central bore 296 which fits over post body 284 which when in combination with post shaft 282 fitting securely into central bore 290 of implant 288, tab 294 fits securely into slot 292 of implant 288. Key 298 is fit into hole 286 when total assembly of post 282, implant 288 and core 300 is complete.

Referring to FIGS. 60-65, the implant 302 includes a central bore 306, tab 308 and a top surface 304 which is not perpendicular to central bore 306 and wall 301 of implant 302. Post 310 has a vertical slot 314 which allows placement of post 310 into central bore of implant 302 such that tab 308 will slide through it, slot 312 allows entry of tab by rotation of post 310 after complete placement of post 310 into central bore 306 of implant 302. Post 310 has a second slot 316. Coping 318 fits securely over post 310 once it is assembled into implant 302 such that surface 304 of implant 302 fits tightly to surface 317 of coping 318 and hole 316 of coping 318 aligns with hole 316 of post 310 to allow placement of key 320. Surface 304 of implant 302 fits securely to surface 317 of coping 318 which are not perpendicular to the path of insertion of post 310 therefore not allowing rotation of post 310 in implant 302.

I claim:

1. A dental system for insertion into a bore of a jaw bone of a patient which comprises:
   a dental implant adapted to fit in a bore of said jaw bone, said dental implant having a central hole extending from a top surface of said implant through a portion of the vertical height of said implant,
   at least one wing extending in a direction selected from the group consisting of (a) into said implant central hole, (b) upward from the top surface of said implant and (c) into said implant central hole and at least one wing extending upward from the top surface of said implant,
   a dental post having a stem section shaped to fit into said central hole and having at least one slot to fit over a wing of said implant,
   and means for positioning said at least on slot onto said at least one wing, said at least one slot and said at least one wing being shaped to prevent rotation of said post in at least one direction after said positioning.

2. The dental system of claim 1 wherein said means for positioning comprises a key adapted for fit within a space in said post thereby to maintain said at least one slot onto said at least one wing.

3. The dental system of claim 1 wherein said means for positioning comprises a key in the form of a coping adapted for fit over said post and said implant thereby to maintain said at least one slot onto said at least one wing.

4. The dental system of claim 3 wherein said means for positioning a key comprises through a slot of said coping and a slot of said post to secure said coping and said post in position.

5. The dental system of any one of claims 1,2,3 or 4 wherein said post has a plurality of slots and said implant has a plurality of wings.

6. The system of any one of claims 1,2,3 or 4 wherein said post has a plurality of slots at essentially the same vertical position.

7. The system of any one of claims 1,2,3 or 4 wherein said at least one slot has a vertical pathway to allow said wing to travel vertically and to be positioned into said slot by rotating said post.

8. The dental system of any one of claims 1,2,3 or 4 wherein said post has at least one slot and said implant has at least one wing.

9. A dental system for insertion into a bore of a jaw bone of a patient which comprises:
a dental implant adapted to fit in a bore of said jaw bone, said dental implant having a central hole extending from a top surface of said implant through a portion of the vertical height of said implant,
at least one slot in said internal surface of said implant, and said slot open to said central hole,
a dental post having a stem section shaped to fit into said central hole and said post having a second central hole extending though a vertical height of said post,
and a key extending through said second central hole and into said slot.

10. The dental system of claim 9 wherein said post has at least one wing extending into or upward from said implant and said post has at least one slot.

11. The system of any one of claim 9 or 10 wherein said post has a plurality of slots and said implant has a plurality of wings.

12. The system of any one of claims 9 or 10 wherein said post has a plurality of slots at essentially the same vertical position.

13. The system of any one of claims 9 or 10 wherein at least one wing has a shape to fit with a vertical pathway in said post and said at least one wing is positioned into said slot by rotating said post.

14. The system of any one of claims 9 or 10 including a coping covering said post to prevent dislodgement of said key.

15. A dental system for insertion into a bore of a jaw bone of a patient which comprises:
a dental implant adapted to fit in a bore of said jaw bone, said dental implant having a central hole extending from a top surface of said implant through a portion of the vertical height of said implant and a bottom internal surface.
at least one slot formed in an internal surface of said implant.
a dental post having a stem section shaped to fit into said central hole, said post forming a second hole with said implant wall and said post wall after placement, said second hole extending the vertical height of said post, and
a key extending through said second hole and into said slot.

16. The system of claim 15 wherein said post has a plurality of slots and a plurality of keys positioned into said slots.

17. The system of claims 15 or 16 wherein said a plurality of slots are at the same vertical height.

18. The system of one of claims 15 or 16 wherein at least one wing has a shape to fit within a vertical pathway in said implant and said at least one wing is positioned into said slot by rotating said post.

19. The system of one of claims 15 or 16 including a coping covering said post to prevent dislodgement of said key.

20. A dental system for insertion into a bore of a jaw bone of a patient which comprises:
a dental implant adapted to fit in a bore of said jaw bone, said dental implant having a central hole extending from a top surface of said implant through a portion of the vertical height of said implant and a bottom internal surface,
at least one slot formed in said bottom internal surface and said slot open to said central hole,
a dental post having a stem section shaped to fit into said central hole, said post and said implant being shaped to form a second central hole extending the vertical height of the post and a key extending through said second hole and into said slot.
a key extending through said second hole and into said slot.

21. The system of claim 20 wherein having a plurality of second holes, and a key for each of said second holes.

22. The system of claim 20 or 21 having a plurality of slots at the same vertical height.

23. The system of one of claims 20 or 21 wherein at least one wing has a shape to fit within a vertical pathway in said post and said at least one wing is positioned into said slot by rotating said post.

24. The system of one of claims 20 or 21 wherein a coping covers said post.

25. A dental system for insertion into a bore of a jaw bone of a patient which comprises:
a dental implant adapted to fit in a bore of said jaw bone, said dental implant having a central hole extending from a top surface of said implant through a portion of the vertical height of said implant and a bottom internal surface, said implant having a wing which extends upward, one said wing having at least one wall angled with respect to a wall of the central hole,
a dental post having a stem section shaped to fit into said central hole,
a coping covering said post and said implant,
and at least one slot formed by a wall of said post and a side of said coping.

26. The system of claim 25 wherein said post has a plurality of slots.

27. The system of claim 25 or 26 wherein said slots are at the same vertical height.

28. A dental system for insertion into a bore of a jaw bone of a patient which comprises:
a dental implant adapted to fit in a bore of said jaw bone, said dental implant having a central hole extending from a top surface of said implant through a portion of the vertical height of said implant and a bottom internal surface, said implant having a slot which extends down from the top surface, one said slot having at least one wall angled with respect to a wall of the central hole,
a dental post having a stem section shaped to fit into said central hole, a coping covering said post and said implant with at least one tab shaped to fit into said at least one slot of said implant.

29. The system of claim 28 wherein said implant has a plurality of slots.

30. The system of claim 28 or 29 wherein said slots are at the same vertical height.

31. A dental system for insertion into a bore of a jaw bone of a patient which comprises:

a dental implant adapted to fit in a bore of said jaw bone, said dental implant having a central hole extending from a top surface of said implant through a portion of the vertical height of said implant and a bottom internal surface, a dental post having a stem section shaped to fit into said central hole, and at least one slot formed by a wall of said post and a wall of said coping, at least one said slot having at least one wall angled with respect to a wall of the central hole, and a coping covering said post and said implant with at least one tab shaped to fit into said at least one slot formed by wall of said implant and a wall of said post.

32. The system of claim 31 wherein said post and implant form a plurality of slots.

33. The system of claim 31 or 32 wherein said slots are at the same vertical height.

* * * * *